(12) United States Patent
DeLuca et al.

(10) Patent No.: US 8,217,023 B2
(45) Date of Patent: Jul. 10, 2012

(54) 19-NOR-VITAMIN D ANALOGS WITH 1,2- OR 3,2-CYCLOPENTENE RING

(75) Inventors: Hector F. DeLuca, Deerfield, WI (US); Agnieszka Glebocka, Madison, WI (US); Lori A. Plum, Arena, WI (US); Margaret Clagett-Dame, Deerfield, WI (US); Rafal R. Sicinski, Warsaw (PL)

(73) Assignee: Wisconsin Alumni Research Foundation, Madison, WI (US)

( * ) Notice: Subject to any disclaimer, the term of this patent is extended or adjusted under 35 U.S.C. 154(b) by 21 days.

(21) Appl. No.: 12/895,540

(22) Filed: Sep. 30, 2010

(65) Prior Publication Data

US 2011/0082122 A1    Apr. 7, 2011

Related U.S. Application Data

(60) Provisional application No. 61/248,126, filed on Oct. 2, 2009.

(51) Int. Cl.
*A61K 31/59* (2006.01)
*C07C 401/00* (2006.01)

(52) U.S. Cl. .................. 514/167; 552/653
(58) Field of Classification Search .............. 514/167; 552/653
See application file for complete search history.

(56) References Cited

U.S. PATENT DOCUMENTS

| | | | |
|---|---|---|---|
| 5,843,928 | A | 12/1998 | Deluca et al. |
| 6,369,099 | B1 | 4/2002 | DeLuca et al. |
| 6,458,827 | B2 | 10/2002 | DeLuca et al. |
| 6,506,912 | B2 | 1/2003 | DeLuca et al. |
| 7,056,904 | B2 | 6/2006 | DeLuca et al. |
| 7,071,179 | B2 | 7/2006 | DeLuca et al. |
| 7,094,776 | B2 | 8/2006 | DeLuca et al. |
| 7,648,974 | B1 * | 1/2010 | DeLuca et al. ............ 514/167 |
| 7,763,598 | B2 * | 7/2010 | DeLuca et al. ............ 514/167 |
| 7,879,829 | B2 * | 2/2011 | DeLuca et al. ............ 514/167 |

OTHER PUBLICATIONS

Glebocka, A et al, "New 1alpha,25-dihydroxy-19-norvitamin D3 Compounds Constrained in a Single A-Ring Conformation: Synthesis of the Analogues by Ring-Closing Metathesis Route and Their Biological Evaluation," Journal of Medicinal Chemistry, American Chemical Society, vol. 52, No. 11, pp. 3496-3504, 2009.

Jeon, H.B. et al, "New A-Ring Analogs of the Hormone 1alpha,25-Dihydroxyvitamin D3: (2-40 -Hydroxymethyl) Tetrahydrofuro [1,2-a]-25-Hydroxyvitamin D3," Tetrahedron, Elsevier Science Publishers, vol. 65, No. 7, pp. 1235-1240, 2009.

Glebocka, A et al, "New 1alpha,25-Dihydroxy-19-Norvitamin D3 Analogs with a Frozen A-Ring Conformation,"Journal of Steroid Biochemistry and Molecular Biology, Elsevier Science LTD., vol. 121, No. 1-2, pp. 46-40, 2010.

\* cited by examiner

*Primary Examiner* — Sabiha Qazi
(74) *Attorney, Agent, or Firm* — Andrus, Sceales, Starke & Sawall, LLP

(57) ABSTRACT

19-nor-vitamin D analogs having an additional cyclopentene ring connecting carbon 1 and carbon 2, or connecting carbon 3 and carbon-2 of the A-ring of the analog, and pharmaceutical uses therefore, are described. These compounds exhibit selective in vitro activities, making them therapeutic agents for the treatment or prophylaxis of some types of cancers, particularly leukemia, colon cancer, breast cancer, skin cancer or prostate cancer.

26 Claims, 3 Drawing Sheets

19-NOR-VITAMIN D ANALOGS WITH 1,2- OR 3,2-CYCLOPENTENE RING

BACKGROUND OF THE INVENTION

This invention relates to vitamin D compounds, and more particularly to 1,2 or 3,2-cyclopentene-19-nor-vitamin D analogs and their pharmaceutical uses.

The natural hormone, 1α,25-dihydroxyvitamin $D_3$ and its analog in ergosterol series, i.e. 1α,25-dihydroxyvitamin $D_2$ are known to be highly potent regulators of calcium homeostasis in animals and humans, and more recently their activity in cellular differentiation has been established, Ostrem et al., Proc. Natl. Acad. Sci. USA, 84, 2610 (1987). Many structural analogs of these metabolites have been prepared and tested, including 1α-hydroxyvitamin $D_3$, 1α-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases as renal osteodystrophy, vitamin D-resistant rickets, osteoporosis, psoriasis, and certain malignancies.

In 1990, a new class of vitamin D analogs was discovered, i.e. the so called 19-nor-vitamin D compounds, characterized by the replacement of the ring A exocyclic methylene group (carbon 19), typical of the vitamin D system, by two hydrogen atoms. Biological testing of such 19-nor-analogs (e.g., 1α,25-dihydroxy-19-nor-vitamin $D_3$) revealed a selective activity profile with high potency in inducing cellular differentiation, with very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Letters 31, 1823 (1990); Perlman et al., Tetrahedron Letters 32, 7663 (1991), and DeLuca et al., U.S. Pat. No. 5,086,191). A few years later, analogs of 1α,25-dihydroxy-19-norvitamin $D_3$ substituted at 2-position with hydroxy or alkoxy groups (DeLuca et al., U.S. Pat. No. 5,536,713) were synthesized. Other 2-substituted analogs of 1α,25-dihydroxy-19-nor-vitamin $D_3$ have also been synthesized, e.g. compounds substituted at 2-position with 2-alkyl groups (DeLuca et al U.S. Pat. No. 5,945,410), and with 2-alkylidene groups (DeLuca et al U.S. Pat. No. 5,843,928). It has been established that they exhibit interesting and selective activity profiles. All these studies indicate that binding sites in vitamin D receptors can accommodate different substituents at C-2 in the synthesized vitamin D analogs.

17-ene vitamin D compounds as well as vitamin D compounds having a double bond in the side chain thereof are also known, and have been proposed for various pharmacological uses. Bone diseases such as osteoporosis, skin disorders such as psoriasis, cancers such as leukemia and cosmetic conditions such as wrinkles are just some of the applications proposed for such compounds. 17-ene compounds are described in U.S. Pat. Nos. 5,545,633; 5,929,056 and 6,399,797 while 2-alkylidene compounds having a side chain with a double bond therein are described in, for example, U.S. Pat. No. 5,843,928.

19-nor vitamin D compounds substituted at the carbon-2 position of ring A with an alkyl group such as methyl, or an alkylidene group such as methylene, and having a side chain lacking one or more of the standard vitamin $D_3$ substitutents, are also known, and have been proposed for various pharmacological uses. For example, numerous 2α-methyl-19,26,27-trinor analogs are described in U.S. Pat. No. 7,241,749 and in U.S. Pat. No. 7,241,909, and numerous 2-methylene-19,26, 27-trinor analogs are described in U.S. Pat. No. 7,244,719. In addition, 2α-methyl-19-nor-(20S)-1α-hydroxy-bishomopregnacalciferol is described in published U.S. Application No. 2007/0254857, and numerous 2-methylene-19,26-dinor vitamin D analogs are described in published U.S. Application No. 2007/0191317 and in published U.S. Application No. 2007/0191316.

19-nor-vitamin D analogs which are characterized by the presence of a methylene substituent at carbon 2 (C-2), a hydroxyl group at carbon 1 (C-1), and a shortened side chain attached to carbon 20 (C-20) have also been synthesized and tested. 1α-hydroxy-2-methylene-19-nor-pregnacalciferol is described in U.S. Pat. No. 6,566,352 while 1α-hydroxy-2-methylene-19-nor-homopregnacalciferol is described in U.S. Pat. No. 6,579,861 and 1α-hydroxy-2-methylene-19-nor-bishomopregnacalciferol is described in U.S. Pat. No. 6,627,622. Their biological activities make these compounds excellent candidates for a variety of pharmaceutical uses, as set forth in the above patents and published patent applications.

In a continuing effort to explore the 19-nor class of pharmacologically important vitamin D compounds, analogs which are characterized by the transposition of the ring A exocyclic methylene group from carbon 10 (C-10) to carbon 2 (C-2), i.e. 2-methylene-19-nor-vitamin D compounds have been recently synthesized and tested (Sicinski et al., J. Med. Chem., 41, 4662 (1998); Sicinski et al., Steroids 67, 247 (2002); DeLuca et al., U.S. Pat. Nos. 5,843,928, 5,936,133 and 6,392,071). Molecular mechanics studies, performed on these analogs, showed that a change of ring-A conformation can be expected resulting in the "flattening" of the cyclohexanediol ring. From molecular mechanics calculations and NMR studies their A-ring conformational equilibrium was established to be ca. 6:4 in favor of the conformer that has an equatorial 1α-OH. Introduction of the 2-methylene group into 19-nor-vitamin D carbon skeleton changes the character of its (1α- and 3β-) A-ring hydroxyls; they are both now in the allylic positions, similar to the 1α-hydroxyl group (crucial for biological activity) in the molecule of the natural hormone, 1α,25-$(OH)_2D_3$. It was found that 1α,25-dihydroxy-2-methylene-19-norvitamin D analogs are characterized by significant biological potency, enhanced dramatically in compounds with an "unnatural" (20S)-configuration.

Very recently, 2-ethylidene analogs of 1α,25-dihydroxy-19-norvitamin $D_3$ have been synthesized. It turned out that such modification of the ring A results in significant biological potency of compounds, especially enhanced in the E-geometrical isomers, Sicinski et al., J. Med. Chem., 45, 3366 (2002). Interestingly, it has been established that E-isomers have A-ring conformational equilibrium considerably shifted to one particular chair form, that possessing 1α-hydroxyl in an equatorial orientation. Also, the analogs which are characterized by the presence of substituted propylidene moiety at C-2 have also been synthesized and preliminary biological tests indicated strong and selective (intestinal) calcemic activity of the E-geometrical isomers.

A-ring conformational equilibrium in vitamin D compounds has attracted considerable research interest for more than 30 years. Development of NMR spectroscopy and force field calculation methods made it possible to establish, or even predict, the proportion of equilibrating α- and β-chair A-ring forms. Parallel to these studies another, closely related problem has been discussed in the literature, namely the correlation of A-ring conformation with biological activities of vitamin D compounds. As early as in 1974 it was proposed [Okamura et al., Proc. Natl. Acad. Sci. USA, 71, 4194 (1974)] that equatorial orientation of 1α-hydroxy group (i.e., the β-chair form) is necessary for the calcium regulation ability. Recently, Moras reported the crystal structures of hVDR ligand binding domain (LBD) bound to the natural hormone [Moras et al, Moll. Cell, 5, 173 (2000)] and the ligands with unnatural configuration at C-20, [Moras et al, Proc. Natl. Acad. Sci. USA, 98, 5491 (2001)] and it became clear that vitamin D receptor binds (at least in the crystalline state) to vitamin D analogs having their A-rings in β-chair conformation. It seemed, therefore, interesting to synthesize a vitamin D analog that could only assume the opposite α-chair conformation of its ring A, and as a consequence, possesses 1α-hydroxy group in the axial orientation.

As a continuation of the search for biologically active 2-alkylidene-19-norvitamin D compounds, analogs which are characterized by the presence of an additional ring and "flattening bond" system [Corey et al, J. Org. Chem., 45, 757 (1980)] have also been synthesized and tested. Such 19-nor-vitamin D compounds seemed interesting targets because structural constrains of their molecules would prevent their ring A from flipping over to the alternative β-chair form, effectively "freezing" the A-ring α-chair conformation.

SUMMARY OF THE INVENTION

The present invention is directed toward 1,2-cyclopentene-19-nor-vitamin D analogs as well as 3,2-cyclopentene-19-nor-vitamin D analogs, their biological activity, and various pharmaceutical uses for these compounds.

A class of vitamin D compounds not known heretofore are the vitamin D isomers having the A-ring exocyclic methylene moiety at C-10 removed and possessing an additional fused cyclopentene ring connecting either C-1 and C-2, or C-3 and C-2. Structurally these novel analogs are characterized by the general formula I and II shown below:

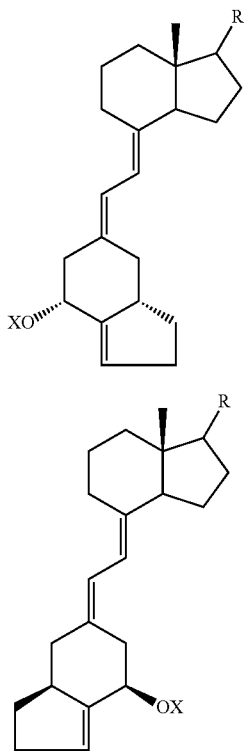

where X is selected from the group consisting of hydrogen and a hydroxy-protecting group, and where the group R represents any of the typical side chains known for vitamin D type compounds. Thus, R may be an alkyl, hydrogen, hydroxyalkyl or fluoroalkyl group, or R may represent a side chain of the formula:

where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

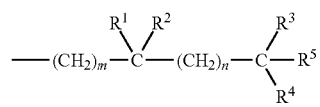

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^5$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group ═CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH— groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

The wavy line to the carbon 20 indicates that carbon 20 may have either the R or S configuration.

Specific important examples of side chains with natural 20R-configuration are the structures represented by formulas (a), b), (c), (d) and (e) below. i.e. the side chain as it occurs in 25-hydroxyvitamin D$_3$ (a); vitamin D$_3$ (b); 25-hydroxyvitamin D$_2$ (c); vitamin D$_2$ (d); and the C-24 epimer of 25-hydroxyvitamin D$_2$ (e).

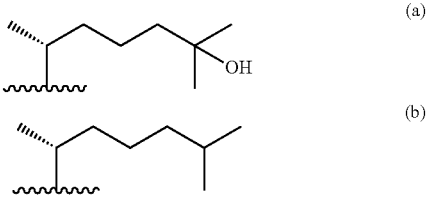

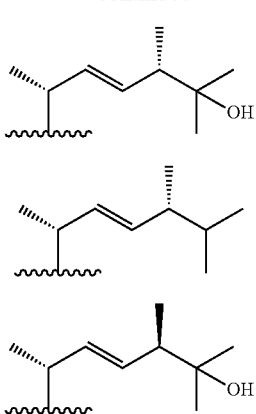

The preferred analog of formula I is 1,2-cyclopentene-25-hydroxy-19-nor-vitamin $D_3$ (hereinafter referred to as "DO-REVA") which has the following formula Ia:

Ia

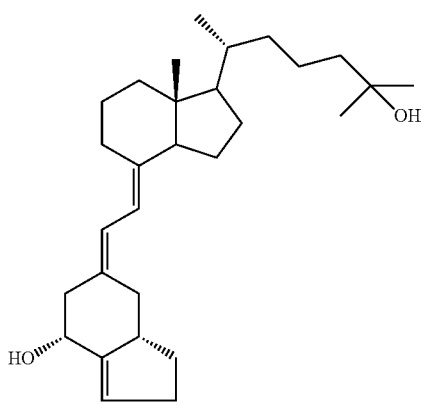

The preferred analog of formula II is 3,2-cyclopentene-1α,25-dihydroxy-19-nor-vitamin D3 (hereinafter referred to as "DO-REVB") which has the following formula IIa:

IIa

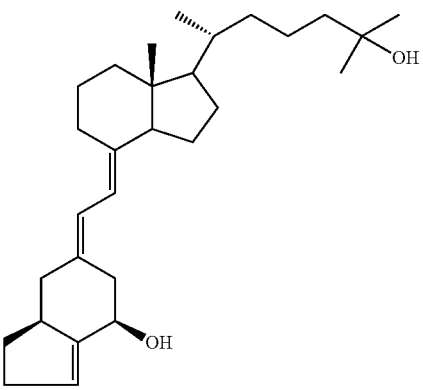

The above compounds I, and particularly Ia, exhibit a desired, and highly advantageous, pattern of biological activity. This compound has markedly reduced in vitro activities. The VDR binding affinity of DO-REVA is significantly lower than the native hormone 1,25(OH)$_2$D$_3$ and in fact can be considered to have little to no receptor binding activity. The potency of DO-REVA to promote HL60 cell differentiation is also significantly less than 1,25(OH)$_2$D$_3$ and it can be considered to have little to no cellular differentiation activity. A similar reduction in potency is observed for the in vitro transcription assay conducted in bone cells. However, DO-REVA does have measurable transcription activity at the higher concentrations tested. It is likely that this compound might serve as a slow-release drug or be used as a local-acting drug coupled with an appropriate delivery method. Such compound might be a useful agent for the treatment or prevention of some types of cancer, especially leukemia, colon cancer, breast cancer, skin cancer or prostate cancer.

The above compounds II, and particularly IIa, exhibit a desired and highly advantageous, pattern of biological activity. DO REVB also has reduced in vitro activities as compared to 1,25(OH)$_2$D$_3$, but its activity is significantly greater than DO-REVA. DO-REVB binds to the nuclear vitamin receptor, but the VDR binding affinity of DO-REVB is approximately 2 logs lower than the native hormone 1,25(OH)$_2$D$_3$. The potency of DO-REVB to promote HL60 cell differentiation is only one log less than 1,25(OH)$_2$D$_3$. A similar reduction in potency is observed for the in vitro transcription assay conducted in bone cells. DO-REVB exhibits a 2 log lower potency than 1,25(OH)$_2$D$_3$ in stimulating gene transactivation. It is likely that this compound might serve as a slow-release drug or be used as a local-acting drug coupled with an appropriate delivery method. Such compound might be a useful agent for the treatment or prevention of some types of cancer, especially leukemia, colon cancer, breast cancer, skin cancer or prostate cancer.

One or more of the compounds may be present in a pharmaceutical composition to treat or prevent the above-noted diseases in an amount from about 0.01 μg/gm to about 1000 μg/gm of the composition, preferably from about 0.1 μg/gm to about 500 μg/gm of the composition, and may be administered topically, transdermally, orally, rectally, nasally, sublingually, or parenterally in dosages of from about 0.01 μg/day to about 1000 μg/day, preferably from about 0.1 μg/day to about 500 μg/day.

BRIEF DESCRIPTION OF THE DRAWINGS

FIG. 1 is a graph illustrating the relative activity of DO-REVA, DO-REVB and 1,25-(OH)$_2$D$_3$ to compete for binding with [$^3$H]-1,25-(OH)$_2$-D$_3$ to the full-length recombinant rat vitamin D receptor;

FIG. 2 is a graph illustrating the percent HL-60 cell differentiation as a function of the concentration of DO-REVA, DO-REVB and 1,25-(OH)$_2$D$_3$; and FIG. 3 is a graph illustrating the in vitro transcription activity of 1,25-(OH)$_2$D$_3$ as compared to DO-REVA and DO-REVB.

DETAILED DESCRIPTION OF THE INVENTION

Figure 1:
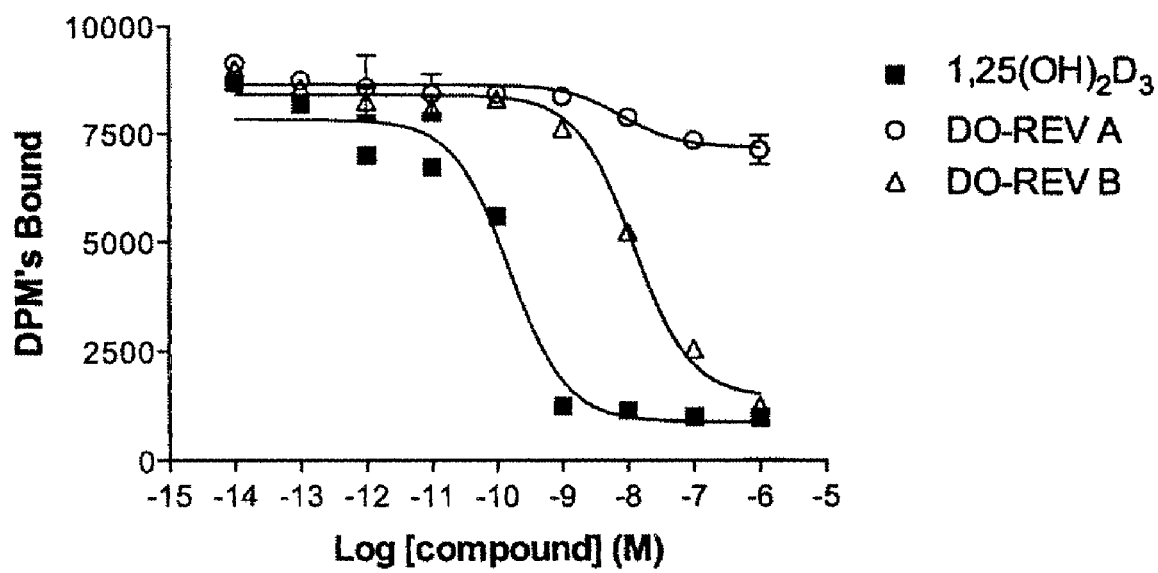
FIGS. 1-3 illustrate various biological activities of 1,2-cyclopentene-25-hydroxy-19-nor-vitamin D$_3$ analog 16, referred to as "DO-REVA," and of 3,2-cyclopentene-1α,25-dihydroxy-19-nor-vitamin D$_3$ analog 15, referred to as "DO-REVB," as compared to the native hormone 1α,25-dihydroxyvitamin D$_3$, hereinafter "1,25(OH)$_2$D$_3$."

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. "Alkoxy" refers to any alkyl radical which is attached by oxygen, i.e. a group represented by "alkyl-O—." Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively. An "alkylidene" refers to a radical having the general formula $C_kH_{2k}$— where k is an integer.

The preparation of 19-nor-vitamin D compounds of the basic structures I and II can be accomplished by a common general method, i.e. the Julia olefination involving a coupling of an unsaturated sulfone IV, easily prepared from a bicyclic Windaus-Grundmann type ketone III, with the bicyclic ketone V:

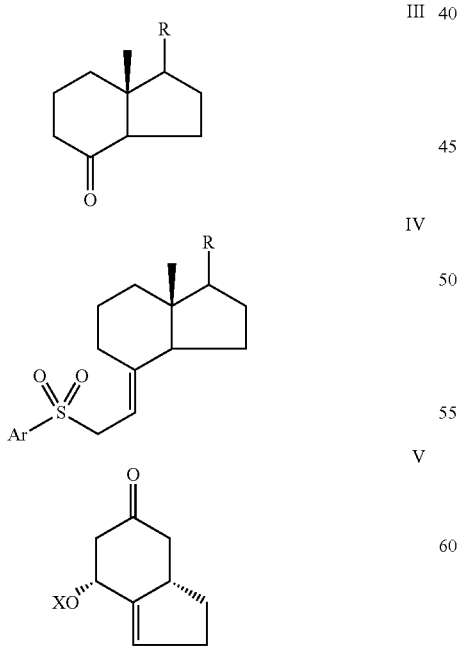

In the structures III, IV and V groups X and R represent groups defined above whereas Ar represents phenyl, substituted phenyl (preferably phenylthiazoline group) and other aromatic groups that can be suitable for the Julia olefination process, it being also understood that any functionalities in Ar that might be sensitive, or that interfere with the condensation reaction, should be avoided. The process shown above represents an application of the convergent synthesis concept, which has been applied effectively for the preparation of vitamin D compounds (e.g. Kittaka et al, Synlett, 8, 1175 (2003), and J. Org. Chem., 68, 7407 (2003).

Hydrindanones of the general structure III are known, or can be prepared by known methods. Specific important examples of such known bicyclic ketones are the structures with the side chains (a), (b), (c) and (d) described above, i.e. 25-hydroxy Grundmann's ketone (e) [Baggiolini et al., J. Org. Chem., 51, 3098 (1986)]; Grundmann's ketone (f) [Inhoffen et al., Chem. Ber. 90, 664 (1957)]; 25-hydroxy Windaus ketone (g) [Baggiolini et al., J. Org. Chem., 51, 3098 (1986)] and Windaus ketone (h) [Windaus et al., Ann., 524, 297 (1936)]:

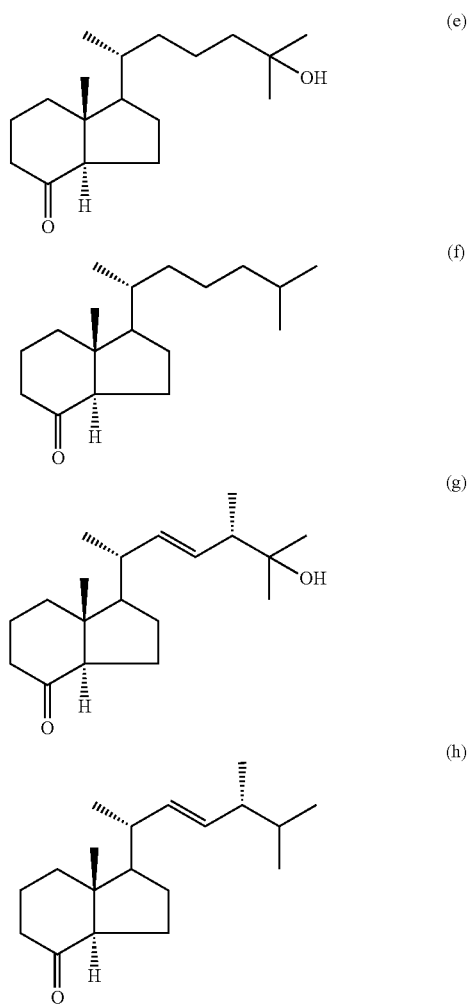

For the preparation of the required bicyclic ketones of general structure V, a new synthetic route has been developed starting from the commercially available (1R,3R,4S,5R)-quinic acid. Process of its transformation into the desired A-ring synthon is shown on the SCHEME I. Thus, in the starting quinic acid, two out of three secondary hydroxyls were protected as a cyclic diacetal and the carboxylic group was methylated. Reaction of the formed bicyclic diol 1 with iodine and triphenylphosphine resulted in formation of a single product, secondary iodide 2, with an inverted configuration at the stereogenic center. The next synthetic step consisted of the radical addition of the iodide 2 to acrylonitrile. The product 3 with equatorial 2'-cyano-ethyl substituent was formed, which was subsequently reduced to the aldehyde 4. Methylenation of the latter was achieved using the rhodium-catalyzed process described by Lebel and Paquet [J. Am. Chem. Soc., 126, 320 (2004)]. In the formed terminal alkene 5 its two vicinal hydroxyls were deprotected and a less hindered one was protected as a silyl ether. The remaining secondary hydroxyl in the diol 7 was oxidized by Dess-Martin periodinane and the formed ketone 8 subjected to Wittig methylenation. The obtained diolefin 9 underwent ring-closing methatesis carried out in a presence of the $2^{nd}$ generation Grubbs catalyst 10. Carbomethoxyl group in the bicyclic product 11 was then reduced with LiAlH4 and the obtained vicinal diol 12 was subjected to periodate oxidation yielding the desired A-ring fragment, protected hydroxycyclohexanone 13. The latter compound was then subjected to modified Julia olefination with the anion generated from thiazoline sulphone 9, prepared from the corresponding Grundmann ketone according to the known procedure [Glebocka et al., J. Med. Chem., 49, 2909 (2006)], and lithium bis(trimethylsilyl)amide. Removal of the silyl protecting groups in the obtained 19-norvitamins gave the expected mixture of two 19-norvitamin D analogs 15 and 16 which were purified and separated by reversed-phase HPLC. Analysis of their NMR spectra confirmed that ring A in these compounds, due to the presence of an exocyclic double bond being a part of additional five-membered ring, is prevented from flipping and held in the single chair conformation. Therefore, in the synthesized vitamins 15 and 16 their secondary hydroxyl (1α or 3β, respectively) can assume only an equatorial orientation.

Several other 19-nor-vitamin D compounds may be synthesized by the method disclosed herein using the A-ring synthon 13 and the appropriate C,D-fragments derived from the Windaus-Grundmann ketones having the desired side chain structure.

This invention is described by the following illustrative examples. In these examples specific products identified by Arabic numerals (e.g. 1, 2, 3, etc.) refer to the specific structures so identified in the preceding description and in the SCHEME I.

EXAMPLES

Chemistry. Melting points (uncorrected) were determined on a Thomas-Hoover capillary melting-point apparatus. Optical rotations were measured in chloroform using a Perkin-Elmer 241 automatic polarimeter at 22° C. Ultraviolet (UV) absorption spectra were recorded with a Perkin-Elmer Lambda 3B UV-VIS spectrophotometer in ethanol. $^1$H nuclear magnetic resonance (NMR) spectra were recorded in deuteriochloroform at 400 and 500 MHz with a Bruker DMX-400 and Bruker DMX-500 spectrometers, respectively. $^{13}$C nuclear magnetic resonance (NMR) spectra were recorded at 100 and 125 MHz with the same spectrometers in deuteriochloroform. Chemical shifts (δ) were reported downfield from internal Me$_4$Si (δ0.00). Electron impact (EI) mass spectra were obtained with a Micromass AutoSpec (Beverly, Mass.) instrument. High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

The starting bicyclic compound 1 was obtained according to the described procedure [Armesto et al., Tetrahedron Letters 41, 8759 (2000)].

Example I

Preparation of Vitamin D Analogues 15 and 16

(a) Conversion of hydroxy compound 1 into iodide 2 (SCHEME I). (2S,3S,4aR,6R,8S,8aS)-6-Hydroxy-8-iodo-2,3-dimethoxy-2,3-dimethyl-octahydro-benzo[1,4]dioxine-6-carboxylic acid methyl ester (2). To a stirred solution of compound 1 (2.84 g, 8.87 mmol) in anhydrous toluene (25 mL) triphenylphosphine (3.40 g, 13.28 mmol), imidazole (1.70 g, 24.26 mmol) and iodine (4.0 g, 16 mmol) were added at room temperature. The mixture was warmed up and stirred at 100-110° C. for 2 h 40 min. Then it was cooled down, poured into aqueous sodium thiosulfate solution and extracted with ethyl acetate. The combined organic phases were washed with water, dried (Na$_2$SO$_4$) and evaporated. The residue was applied on a silica column. Elution with hexane/ethyl acetate (7:3) resulted in pure compound 2 (2.00 g, 53%).

2: $^1$H NMR (500 MHz, CDCl$_3$) δ 1.30 and 1.36 (3H and 3H, each s, 2- and 3-H$_3$), 1.92 (1H, dm, J ~12.5 Hz, 5α-H), 2.03 (1H, t, J=12.4 Hz, 5β-H), 2.39 (1H, dm, J=13.2 Hz, 7α-H), 2.49 (1H, t, J ~13 Hz, 7β-H), 3.25 and 3.38 (3H and 3H, each s, 2×OCH$_3$), 3.62 (1H, t, J=10.4 Hz, 8aβ-H), 3.81 (3H, s, COOCH$_3$), 3.98 (1H, m, 8α-H), 4.25 (1H, br dt, J=~4, ~11.5 Hz, 4aα-H); HRMS (ESI) exact mass calcd for C$_{14}$H$_{23}$O$_7$Na (M+Na)$^+$ 453.0386, measured 453.0390.

(b) Radical addition of iodide 2 with acrylonitrile. (2S,3S,4aR,6S,8S,8aR)-8-(2'-Cyano-ethyl)-6-hydroxy-2,3-dimethoxy-2,3-dimethyl-octahydro-benzo[1,4]dioxine-6-carboxylic acid methyl ester (3). To a solution of iodide 2 (863 mg, 2.01 mmol), acrylonitrile (1.33 mL) and AIBN (66 mg, 0.40 mmol) in anhydrous toluene (4.5 mL) at 70° C., tributyltin hydride (0.994 mL, 3.61 mmol) was slowly added. The solution was heated at 100-110° C. for 2 h. Then it was cooled down, shaken with an aqueous solution of sodium tiosulfate and extracted with ethyl acetate. The combined organic phases were washed with water, dried (Na$_2$SO$_4$) and evaporated. The remaining residue was applied on a silica column. Elution with hexane/ethyl acetate (6:4) resulted in pure compound 3 (485 mg, 67%).

3: $^1$H NMR (500 MHz, CDCl$_3$) δ 1.28 and 1.32 (3H and 3H, each s, 2- and 3-H$_3$), 1.45-1.53 (1H, m, one of 1'-H$_2$), 1.56 (1H, t, J ~13 Hz, 7β-H), 1.75 (1H, dt, J=13.2, 2.8 Hz, 7α-H), 1.85 (1H, ddd, J=12.6, 4.8, 2.4 Hz, 5α-H), 1.92 (1H, t, J ~12 Hz, 5β-H), 1.97-2.04 (1H, m, one of 1'-H$_2$), 2.18 (1H, br m, 8α-H), 3.249 and 3.253 (3H and 3 1-1, each s, 2×OCH$_3$), 3.32 (1H, t, J ~10 Hz, 8aβ-H), 2.36-2.53 (2H, m, 2'-H$_2$), 3.79 (3H, s, COOCH$_3$), 3.97 (1H, ddd, J=11.7, 9.8, 4.8 Hz, 4aα-H); $^{13}$C NMR (125 MHz) δ 15.2, 17.69, 17.71, 27.8, 34.5, 37.8, 39.0, 47.8, 47.9, 53.1, 66.7, 73.4, 75.0, 99.3, 99.7, 119.8, 175.9; HRMS (ESI) exact mass calcd for C$_{17}$H$_{27}$O$_7$Na (M+Na)$^+$ 380.1685, measured 380.1677.

(c) Reduction of nitrile 3 to aldehyde 4. (2S,3S,4aR,6S,8S,8aR)-6-Hydroxy-2,3-dimethoxy-2,3-dimethyl-8-(3'-oxo-propyl)-octahydro-benzo[1,4]dioxine-6-carboxylic acid methyl ester (4). DIBALH (1.0 M solution in toluene, 0.54 mL) was added at −70° C. to a solution of nitrile 3 (61 mg, 0.17 mmol) in anhydrous toluene (2.9 mL). The solution was allowed to warm up to −30° C. during 70 min, then stirring was continued for additional 15 min at −30-−40° C. Saturated aqueous solution of ammonium chloride was added, the mixture was poured into brine containing 2% HCl and extracted with ethyl acetate. The combined organic phases were washed with brine, dried (Na$_2$SO$_4$) and evaporated. The remaining residue was applied on a silica column. Elution with hexane/ethyl acetate (6:4) resulted in pure compound 4 (20 mg, 33%).

4: $^1$H NMR (400 MHz, CDCl$_3$) δ 1.29 and 1.32 (3H and 3H, each s, 2- and 3-H$_3$), 1.42 (1H, m, one of 1'-H$_2$), 1.53 (1H, t, J ~13 Hz, 7β-H), 1.74 (1H, dt, J=13.1, 2.6 Hz, 7α-H), 1.84 (1H, ddd, J=12.6, 4.7, 2.6 Hz, 5α-H), 1.89-2.02 (1H, m, one of 1'-H$_2$; overlapped with 5β-H), 1.93 (1H, t, J ~12 Hz, 5β-H), 2.16 (1H, br m, 8α-H), 2.52 (2H, t, J=7.8 Hz, 2'-H$_2$), 3.25 and 3.26 (3H and 3H, each s, 2×OCH$_3$), 3.32 (1H, t, J ~10 Hz, 8aβ-H), 3.79 (3H, s, COOCH$_3$), 3.97 (1H, ddd, J=11.7, 9.8, 4.7 Hz, 4aα-H), 9.77 (1H, s, CHO); $^{13}$C NMR (100 MHz) δ 17.73, 17.76, 23.18, 27.8, 34.5, 37.9, 39.2, 41.7, 47.8, 47.9, 53.1, 66.9, 73.6, 74.9, 99.3, 99.6, 175.9, 176.2, 202.2; HRMS (ESI) exact mass calcd for C$_{17}$H$_{28}$O$_8$Na (M+Na)$^+$ 383.1691, measured 383.1692.

(d) Methylenation of aldehyde 4. (2S,3S,4aR,6S,8S,8aR)-8-(But-3'-enyl)-6-hydroxy-2,3-dimethoxy-2,3-dimethyl-octahydro-benzo[1,4]dioxine-6-carboxylic acid methyl ester (5). To a stirred solution of (PPh$_3$)$_3$RhCl (~1 mg, 1 μmol) and Ph$_3$P (21 mg, 78.5 μmol) in anhydrous THF (0.2 mL) at room temperature under argon, 2-propanol (60 μL) was added followed by a solution of aldehyde 4 (26 mg, 72 μmol) in anhydrous THF (0.3 mL) and Me$_3$SiCHN$_2$ (2 M solution in hexane; 60 μL, 120 μmol). The solution was stirred at room temperature for 6 h, H$_2$O$_2$ was added (5%, 0.5 mL) and the mixture was poured into brine and extracted with methylene chloride. The combined organic phases were washed with brine, dried (Na$_2$SO$_4$) and evaporated. The residue was applied on a silica column. Elution with hexane/ethyl acetate (7:3) gave pure compound 5 (5.5 mg, 21%).

5: $^1$H NMR (500 MHz, CDCl$_3$) δ 1.13 (1H, m), 1.29 and 1.32 (3H and 3H, each s, 2-CH$_3$ and 3-CH$_3$), 1.49 (1H, t, J=13.0 Hz, 7β-H), 1.81-1.85 (2H, m), 1.89-2.03 (3H, m, overlapped with 5β-H), 1.94 (1H, t, J ~12.5 Hz, 5β-H), 2.12 (1H, m, 8α-H), 3.25 (6H, s, 2×OCH$_3$), 3.29 (1H, t, J ~10 Hz, 8aβ-H), 3.79 (3H, s, COOCH$_3$), 3.97 (1H, ddd, J=12.0, 9.8, 4.6 Hz, 4aα-H), 4.93 (1H, d, J=10.0 Hz, 4'-H$_{trans}$), 4.99 (1H, dd, J=17.0, 1.1 Hz, 4'-H$_{cis}$), 5.80 (1H, m, 3'-H); $^{13}$C NMR (125 MHz) δ 17.77, 17.82, 29.9, 30.8, 34.5, 37.9, 39.0, 47.8, 47.9, 53.0, 67.1, 73.8, 74.7, 99.3, 99.6, 114.4, 138.7, 176.5.

(e) Hydrolysis of ether protecting group in compound 5. (1S,3R, 4R, 5S)-5-(But-3'-enyl)-1,3,4,-trihydroxy-cyclohexanecarboxylic acid methyl ester (6). A solution of compound 5 (14 mg, 39 μmol in trifluoroacetic acid/water (5:1, 2 mL) was stirred at room temperature for 1 h, poured into aqueous saturated sodium bicarbonate solution and extracted with ethyl acetate. The combined organic phases were washed with brine, dried (Na$_2$SO$_4$) and evaporated. The residue was applied on a Sep-Pak (2 g). Elution with hexane/ethyl acetate (3:7) gave pure triol 6 (5.5 mg, 58%).

6: $^1$H NMR (500 MHz, CDCl$_3$) δ 1.28 (1H, m, one of 1'-H$_2$), 1.54 (1H, t, J ~13 Hz, 6β-H), 1.79 (1H, dt, J=13.6, 3.1 Hz, 6α-H), 1.82 (1H, t, J ~12 Hz, 2β-H), 1.87-L96 (2H, m, 2α-H overlapped with one of 1'-H$_2$), 2.02 (2H, narr m, 2'-H$_2$), 2.14 (1H, br m, 5α-H), 3.15 (1H, t, J ~9.5 Hz, 4β-H), 3.80 (3H, s, COOCH$_3$), 3.83 (1H, ddd, J=11.9, 9.2, 4.8 Hz, 3α-H), 4.96 (1H, d, J=9.9 Hz, 4'-H$_{trans}$), 5.02 (1H, dd, J=17.1, 1.1 Hz, 4'-H$_{cis}$), 5.81 (1H, m, 3'-H); $^{13}$C NMR (125 MHz) δ 30.59, 30.62, 36.8, 38.6, 40.6, 53.1, 71.5, 73.9, 78.9, 114.7, 142.9, 176.4; HRMS (ESI) exact mass calcd for C$_{12}$H$_{20}$O$_5$Na (M+Na)$^+$ 267.1208, measured 267.1217.

(f) Selective protection of one of hydroxyl groups in diol 6. (1S,3R,4R,5S)-5-(But-3'-enyl)-3-[(tert-butyldimethylsilyl)oxy]-1,4-dihydroxy-cyclohexanecarboxylic acid methyl ester (7). tert-Butyldimethylsilyl chloride (16 mg, 0.11 mmol) was added at 5° C. to a solution of diol 6 (25 mg, 0.102 mmol) and imidazole (23 mg, 0.331 mmol) in anhydrous DMF and it was stirred at room temperature for 2.5 h, poured into brine and extracted with ethyl acetate. The organic phase was washed with brine, dried (Na$_2$SO$_4$) and evaporated. The residue was applied on a Sep-Pak (2 g). Elution with hexane/ethyl acetate (95:5) gave pure compound 7 (18 mg, 50%). Further elution with hexane/ethyl acetate (8:2) provided the unreacted substrate 6 (1.5 mg).

7: $^1$H NMR (500 MHz, CDCl$_3$) δ 0.082 and 0.112 (2×3H, 2×s, 2×SiCH$_3$), 0.895 (9H, s, Si-t-Bu), 1.27 (1H, m, one of 1'-H$_2$), 1.53 (1H, t, J ~13 Hz, 6β-H), 1.76 (1H, dt, J=13.5, ~3 Hz, 6α-H), 1.80 (1H, t, J ~11 Hz, 2β-H), 1.87 (1H, ddd, J=12.6, 4.8, 2.6 Hz, 2α-H), 1.90-1.96 (3H, m, 2'-H$_2$ overlapped with one of 1'-H$_2$), 2.15 (1H, br m, 5α-H), 3.15 (1H, t, J ~9.5 Hz, 4β-H), 3.79 (3H, s, COOCH$_3$), 3.82 (1H, ddd, J=10.9, 8.4, 4.8 Hz, 3α-H), 4.94 (1H, d, J=10.0 Hz, 4'-H$_{trans}$), 5.01 (1H, dd, J=16.8, 1.6 Hz, 4'-H$_{cis}$), 5.81 (1H, m, 3'-H); $^{13}$C NMR (125 MHz) δ-4.7, -42, 18.0, 25.8, 30.6, 30.8, 36.1, 38.6, 41.3, 53.1, 72.8, 74.1, 78.6, 114.4, 138.7, 176.6.

(g) Oxidation of hydroxy group in compound 7. (1S,3R, 5S)-5-But-3-enyl-3-[(tert-butyldimethylsilyl)oxy]-1-hydroxy-4-oxo-cyclohexanecarboxylic acid methyl ester (8). Dess-Martin periodinane (20 mg, 68 μmol) was added at room temperature to a solution of diol 7 (12 mg, 32 mop in anhydrous methylene chloride (0.3 mL). The solution was stirred at room temperature for 24 h, then poured into brine/diluted sodium bicarbonate and extracted with ethyl acetate. The organic phase was washed with brine, dried (Na$_2$SO$_4$) and evaporated. The residue was applied on a Sep-Pak (2 g). Elution with hexane/ethyl acetate (95:5) gave pure ketone 8 (10.5 mg, 88%).

8: $^1$H NMR (400 MHz, CDCl$_3$) δ 0.017 and 0.137 (2×3H, 2×s, 2×SiCH$_3$), 0.910 (9H, s, Si-t-Bu), 1.30 (1H, m, one of 1'-H$_2$), 1.90 (1H, t, J=13.2 Hz, 6β-H), 1.96-2.10 (4H, m, 6α-H overlapped with 2α-H and 2'-H$_2$), 2.22 (1H, t, J=12.8 Hz, 2β-H), 2.26 (1H, m, one of 1'-H$_2$), 2.84 (1H, m, 5α-H), 3.81 (3H, s, COOCH$_3$), 4.60 (1H, dd, J=11.2, 7.2 Hz, 3α-H), 4.96 (1H, d, J=11.2 Hz, 4'-H$_{trans}$), 5.00 (1H, d, J=18.8 Hz, 4'-H$_{cis}$), 5.77 (1H, m, 3'-H); HRMS (ESI) exact mass calcd for C$_{18}$H$_{32}$O$_5$NaSi (M+Na)$^+$ 379.1917, measured 379.1912.

(h) Wittig reaction with ketone 8. (1S,3R,5S)-5-(But-3'-enyl)-3-[(tert-butyldimethylsily)oxy]-1-hydroxy-4-methylene-cyclohexanecarboxylic acid methyl ester (9). To the methyltriphenylphoshonium bromide (26 mg, 72 μmol) in anhydrous THF (0.1 mL) at 0° C. was added dropwise n-BuLi (1.6 M in hexanes; 74 μL, 74 μmol) under argon with stirring. The solution was stirred at 0° C. for 10 min and then the orange-red mixture was cooled to −78° C. and siphoned to a solution of ketone 8 (7.5 mg, 24 μmol) in anhydrous THF (100 μL). The reaction mixture was allowed to warm up to −12° C. during 1 h and stirring was continued for additional 40 min at −12--20° C. Few drops of 1% HCl were added followed by ethyl acetate (3 mL) and aqueous saturated sodium bicarbonate (2 mL). The mixture was vigorously stirred at room temperature for 10 min. Then an organic phase was separated, washed with brine, dried (MgSO$_4$), and evaporated. The oily residue was purified by filtration through a silica Sep-Pak (0.5 g). Elution with hexane/ethyl acetate (95:5) resulted in pure olefinic product 9 (4.5 mg, 60%).

9: $^1$H NMR (400 MHz, CDCl$_3$) δ 0.061 and 0.071 (2×3H, 2×s, 2×SiCH$_3$), 0.916 (9H, s, Si-t-Bu), 1.30-1.40 (1H, m, one of 1'-H$_2$), 1.49 (1H, t, J ~13 Hz, 6β-H), 1.81 (2H, m, 6α-H overlapped with 2β-H), 1.82 (1H, t, J ~12 Hz, 2β-H), 2.00 (1H, ddd, J=12.5, 4.8, 2.4 Hz, 2α-H), 2.04-2.15 (3H, m, one of 1'-H$_2$ overlapped with 2'-H$_2$), 2.37 (1H, m, w/2=24 Hz, 5α-H), 3.37 (1H, dd, J=11.2, 4.8 Hz, 3α-H), 3.77 (3H, s, COOCH$_3$), 4.78 and 5.18 [2×1H, 2×s, H$_2$C=C(4)], 4.94 (1H, d, J=10.0 Hz, 4'-H$_{trans}$), 5.01 (1H, d, J=17.1 Hz, 4'-H$_{cis}$), 5.81 (1H, m, 3'-H).

(i) Ring closing methathesis of diolefin 9. (3aS,5S,7R)-7-[(tert-Butyldimethylsilyl)oxy]-5-hydroxy-2,3a,4,5,6,7-hexahydro-3H-indene-5-carboxylic acid methyl ester (11). A solution of diolefin 9 (4 mg, 11.3 μmol) and Grubbs catalyst II generation (10, 1.2 g, 1.5 μmol) in anhydrous toluene (3 mL) was stirred at 80° C. for 1 h, cooled to room temperature, concentrated and purified by silica Sep-Pak (2 g). Elution with hexane/ethyl acetate (95:5) resulted in pure bicyclic product (3 mg, 82%).

11: $^1$H NMR (400 MHz, CDCl$_3$) δ 0.072 and 0.090 (2×3H, 2×s, 2×SiCH$_3$), 0.916 (9H, s, Si-t-Bu), 1.47 (1H, m, one of 3-H$_2$), 1.51 (1H, t, J ~12.5 Hz, 4β-H), 1.77 (1H, t, J=11.5 Hz, 6β-H), 1.87 (1H, ddd, J=12.8, 5.5, 2.2 Hz, 4α-H), 1.95 (1H, ddd, J=12.5, 5.7, 2.2 Hz, 6α-H), 2.20 (1H, m, one of 3-H$_2$), 2.36 (2H, m, 2-H$_2$), 2.96 (1H, m, w/2=24 Hz, 3aα-H), 3.77 (3H, s, COOCH$_3$), 4.55 (1H, m, w/2=23 Hz, 7α-H), 5.55 (1H, narr m, 1-H); HRMS (ESI) exact mass calcd for C$_{17}$H$_{30}$O$_4$NaSi (M+Na)$^+$ 349.1811, measured 349.1805.

(j) Reduction of ester 11. (3aS,5S,7R)-7-[(tert-Butyldimethylsilyl)oxy]-5-hydroxymethyl-2,3a,4,5,6,7-hexahydro-3H-inden-5-ol (12). Lithium aluminum hydride (10 mg, 0.26 mmol) was added at 0° C. to a solution of ester 11 (1.5 mg, 4.6 μmol) in anhydrous THF (0.25 mL). The suspension was stirred at room temperature for 70 min and saturated ammonium chloride was added. The mixture was extracted with ethyl acetate. The combined organic phases were washed with brine, dried (Na$_2$SO$_4$) and evaporated. The residue was applied on a Sep-Pak (0.5 g). Elution with hexane/ethyl acetate (7:3) resulted in pure diol 12 (1.2 mg, 81%).

12: $^1$H NMR (400 MHz, CDCl$_3$) δ 0.087 and 0.100 (2×3H, 2×s, 2×SiCH$_3$), 0.923 (9H, s, Si-t-Bu), 1.02 (1H, t, J=12.7 Hz, 4β-H), 1.26 (1H, t, J ~12 Hz, 6β-H), 1.45 (1H, m, one of 3-H$_2$), 1.91 (1H, ddd, J=~13, 5.7, 2.4 Hz, 4α-H), 2.01 (1H, ddd, J=12.8, 5.8, 2.4 Hz, 6α-H), 2.21 (1H, m, one of 3-H$_2$), 2.36 (2H, m, 2-H$_2$), 2.92 (1H, m, w/2=25 Hz, 3aα-H), 3.43 (2H, narr m, CH$_2$OH), 4.55 (1H, m, w/2=23.5 Hz, 7α-H), 5.55 (1H, t, J ~3 Hz, 1-H).

(k) Cleavage of vicinal diol 12. (3aS,7R)-7-[(tert-Butyldimethylsilyl)oxy]-2,3,3a,4,6,7-hexahydro-inden-5-one (13). Sodium periodate-saturated water (0.1 mL) was added to a solution of the diol 12 (1.1 mg, 3.7 μmol) in methanol (0.4 mL) at 0° C. The solution was stirred at 0° C. for 1 h, poured into brine, and extracted with ethyl acetate and ether. The extract was washed with brine, dried (Na$_2$SO$_4$), and evaporated. A remaining residue was redissolved in hexane/CH$_2$Cl$_2$ and applied on a Sep-Pak (0.5 g). Pure ketone 13 (1 mg, ~95%) was eluted with hexane/ethyl acetate (95:5).

(l) Julia coupling of ketone 13 with sulfone 14. 1α,25-Dihydroxyvitamin D analog 15 and 25-hydroxyvitamin D analog 16. To a solution of sulfone 14 (17.0 mg, 28 μmol) in dry THF (150 μL), LiHMDS (1 M in THF; 30 μL, 30 μmol) was added at −78° C. under argon. The solution turned deep red. The mixture was stirred at −78° C. for 5 min, and a solution of ketone 13 (1 mg, 3.8 μmol) in THF (100+80 μL) was added. The reaction mixture was allowed to warm to −20° C. during 2 h. Then brine containing 1% HCl was added, the mixture was poured into brine and extracted with ethyl acetate. The extract was washed with brine, dried (Na$_2$SO$_4$), and evaporated. The yellow oily residue was applied on a silica column, eluted with hexane/ethyl acetate (98:2) and concentrated under vacuum. The oily product was dissolved in anhydrous THF (1.8 mL) and treated with TBAF (1 M in THF; 80 μL, 80 μmol) and Et$_3$N (8 μL). The solution was stirred at room temperature under argon for 19 h, poured into brine, and extracted with ethyl acetate. The extract was washed with brine, dried (Na$_2$SO$_4$) and evaporated. The obtained products were separated by reversed-phase HPLC (9.4 mm×25 cm Zorbax Eclipse XDB column, 4 mL/min) using methanol/water (95:5) solvent system: 25-hydroxyvitamin D analog 16 (133 μg) was collected at R$_V$ 29.5 mL and isomeric 1α,25-dihydroxyvitamin D analog 15 (292 μg) at R$_V$ 45 mL.

15: UV (in EtOH) λ$_{max}$ 245.0, 252.5, 261.5 nm; $^1$H NMR (500 MHz, CDCl$_3$) δ 0.549 (3H, s, 18-H$_3$), 0.939 (3H, d, J=6.4 Hz, 21-H$_3$), 1.220 (6H, s, 26- and 27-H$_3$), 1.74 (1H, br t, J ~12 Hz, 10α-H), 1.81 (1H, br t, J ~12 Hz, 4α-H), 2.00 [2H, m, CH$_2$—CH$_2$—CH=C(2)], 2.20 [1H, dt, J=8.4, 3.9 Hz, one of CH$_2$—CH=C(2)], 2.35 [1H, br m, one of CH$_2$—CH=C(2)], 2.45 (1H, dd, J=12.5, 5.6 Hz, 4β-H), 2.53 (1H, br m, 3β-H), 2.81 (1H, br d, J=12.5 Hz, 9β-H), 3.24 (1H, dd, J=12.1, 5.1 Hz, 10β-H), 4.12 (1H, m, w/2=21.5 Hz, 1β-H), 5.56 (1H, narr m, CH=C(2)), 5.89 and 6.23 (1H and 1H, each d, J=11.2 Hz, 7- and 6-H; HRMS (ESI) exact mass calcd for C$_{29}$H$_{46}$O$_2$Na (M+Na)$^+$ 449.3396, measured 449.3395.

16: UV (in EtOH)λ$_{max}$ 245.0, 253.0, 262.0 nm; $^1$H NMR (500 MHz, CDCl$_3$) δ 0.569 (3H, s, 18-H$_3$), 0.945 (3H, d, J=6.4 Hz, 21-H$_3$), 1.221 (61-1, s, 26- and 27-H$_3$), 2.02 [2H, m, CH$_2$—CH$_2$—CH=C(2)], 2.25 [1H, m, one of CH$_2$CH=C(2)], 2.55 (1H, m, w/2=24 Hz, 1α-H), 2.65 (1H, dd, J=11.7, 5.7 Hz, 4α-H), 2.81 (1H, br d, J=13.1 Hz, 9β-H), 2.99 (1H, dd, J=12.8, 5.4 Hz, 10α-H), 4.19 (1H, m, w/2=22.5 Hz, 3α-H), 5.57 [1H, narr m, CH=C(2)], 5.84 and 6.19 (1H and 1H, each d, J=11.2 Hz, 7- and 6-H).

SCHEME I

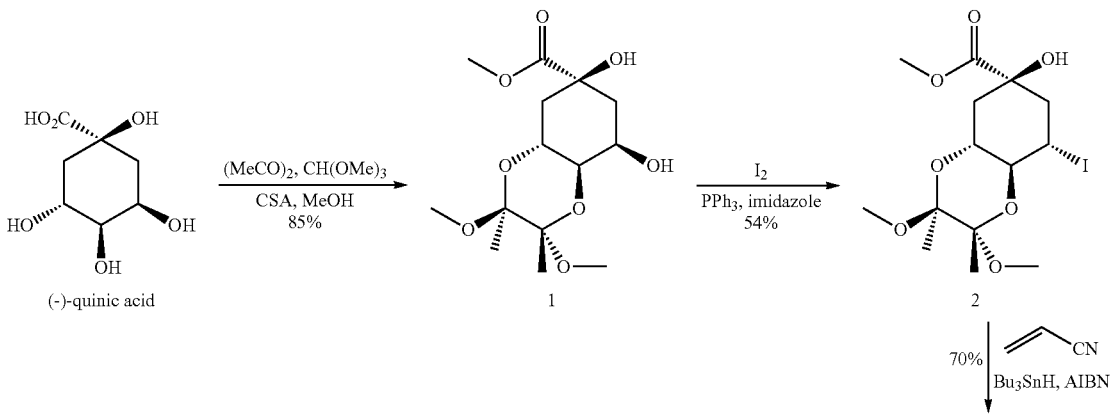

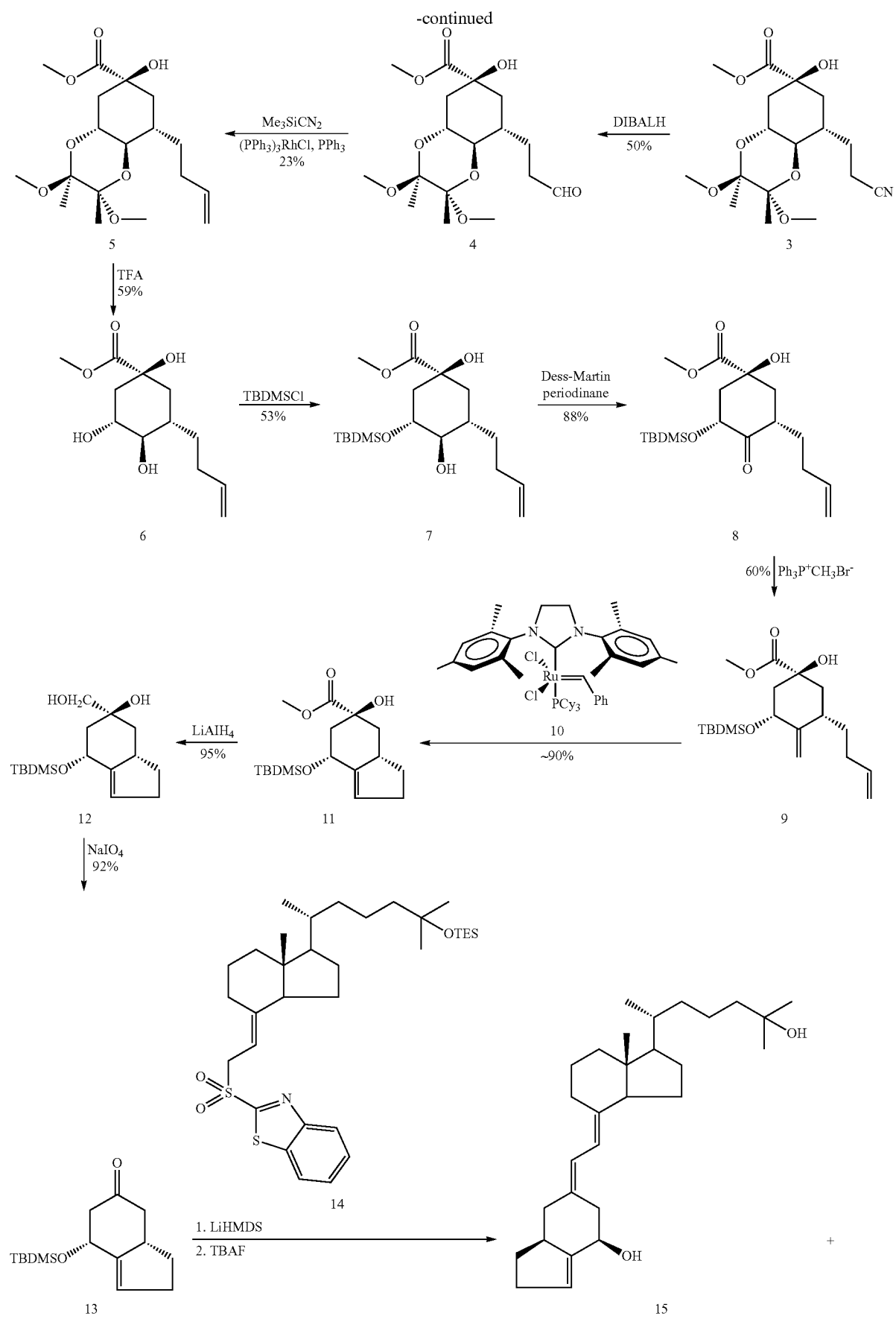

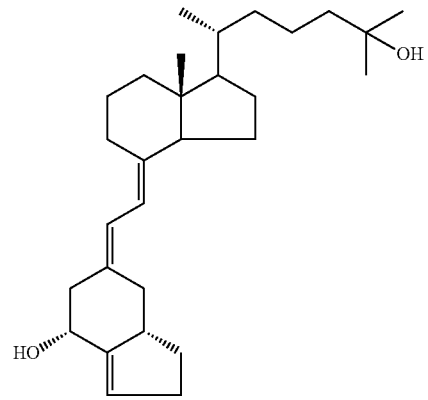

16

Biological Activity of 1,2-Cyclopentene-25-Hydroxy-19-Nor Vitamin D₃ (Analog 16, DO-REVA)

The introduction of a fused cyclopentene ring connecting carbon-1 and carbon-2 (analog 16, DO-REVA) significantly diminished binding to the full length recombinant rat vitamin D receptor, as compared to 1α,25-dihydroxyvitamin D₃. FIG. 1 illustrates that DO-REVA has little to no receptor binding activity.

Figure 2:
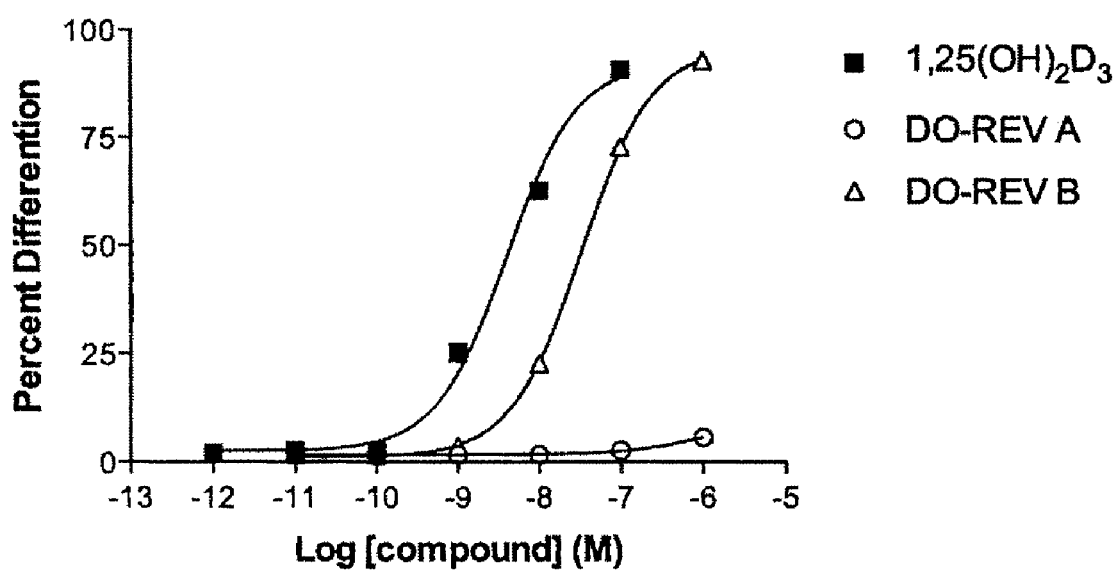

FIG. 2 illustrates that DO-REVA is considerably less active than 1,25-(OH)₂D₃ on HL-60 cell differentiation. The data show it has little to no cellular differentiation activity.

Figure 3:
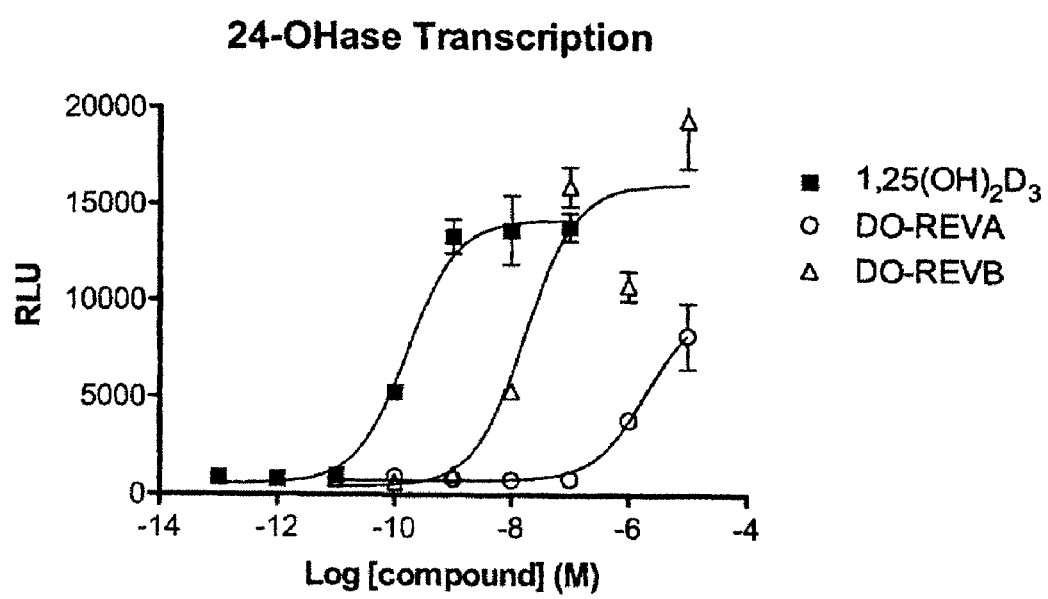

FIG. 3 illustrates that the compound DO-REVA has much less transcriptional activity than 1α,25-dihydroxyvitamin D₃ in bone cells. However, DO-REVA does have measurable transcriptional activity at the higher concentrations tested.

Although not as potent as 1α,25-(OH)₂D₃, DO-REVA still has cell differentiation activity, and thus the activity of DO-REVA on cell differentiation suggests that DO-REVA may be a candidate for the treatment of a cancer, especially against leukemia, colon cancer, breast cancer, skin cancer and prostate cancer.

FIG. 3 illustrates that in bone cells the compound DO-REVA has some ability to increase transcription of the 24-hydroxylase gene. This result, together with the cell differentiation activity of FIG. 2, further suggests that DO-REVA may have significant activity as an anti-cancer agent, especially against leukemia, colon cancer, breast cancer, skin cancer and prostate cancer, because it has direct cellular activity in causing cell differentiation, gene transcription, and in suppressing cell growth.

Biological Activity Of 3,2-Cyclopentene-1α,25-Dihydroxy-19-Nor Vitamin D₃ (Analog 15, DO-REVB)

The introduction of a fused cyclopentene ring connecting carbon-3 and carbon-2 (analog 15, DO-REVB) diminished binding to the full length recombinant rat vitamin D receptor, as compared to 1α,25-dihydroxyvitamin D₃. FIG. 1 illustrates that DO-REVB binds to the nuclear vitamin D receptor, but with an affinity that is 2 logs lower than 1,25(OH)₂D₃.

FIG. 2 illustrates that DO-REVB is almost as active as 1,25-(OH)₂D₃ on HL-60 cell differentiation. The data show it is only about 1 log less active than 1,25(OH)₂D₃.

FIG. 3 illustrates that the compound DO-REVB has less transcriptional activity than 1α,25-dihydroxyvitamin D₃ in bone cells. However, DO-REVB exhibits only a 2-fold lower potency than the native hormone in stimulating gene transactivation.

Although not as potent as 1α,25-(OH)₂D₃, DO-REVB still has cell differentiation activity, and thus the activity of DO-REVB on cell differentiation suggests that DO-REVB may be a candidate for the treatment or prevention of a cancer, especially against leukemia, colon cancer, breast cancer, skin cancer and prostate cancer.

FIG. 3 illustrates that in bone cells the compound DO-REVB has some ability to increase transcription of the 24-hydroxylase gene. This result, together with the cell differentiation activity of FIG. 2, further suggests that DO-REVB may have significant activity as an anti-cancer agent, especially against leukemia, colon cancer, breast cancer, skin cancer and prostate cancer, because it has direct cellular activity in causing cell differentiation, gene transcription, and in suppressing cell growth.

Experimental Methods

Vitamin D Receptor Binding
Test Material
Protein Source

Full-length recombinant rat receptor was expressed in *E. coli* BL21 (DE3) Codon Plus RTL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in $TEDK_{50}$ (50 mM Tris, 1.5 mM EDTA, pH7.4, 5 mM DTT, 150 mM KCl) with 0.1% Chaps detergent. The receptor protein and ligand concentration were optimized such that no more than 20% of the added radiolabeled ligand was bound to the receptor.

Study Drugs

Unlabeled ligands were dissolved in ethanol and the concentrations determined using UV spectrophotometry (1,25-(OH)₂D₃: molar extinction coefficient=18,200 and $\lambda_{max}$=265 nm; Analogs: molar extinction coefficient=42,000 and $\lambda_{max}$=252 nm). Radiolabeled ligand (³H-1,25-(OH)₂D₃, ~159 Ci/mmole) was added in ethanol at a final concentration of 1 nM.

Assay Conditions

Radiolabeled and unlabeled ligands were added to 100 mcl of the diluted protein at a final ethanol concentration of $\leq 10\%$, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material

Study Drugs

The study drugs were dissolved in ethanol and the concentrations determined using UV spectrophotometry. Serial dilutions were prepared so that a range of drug concentrations could be tested without changing the final concentration of ethanol ($\leq 0.2\%$) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2 \times 10^5$ cells/ml. Eighteen hours after plating, cells in duplicate were treated with drug. Four days later, the cells were harvested and a nitro blue tetrazolium reduction assay was performed (Collins et al., 1979; J. Exp. Med. 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer.

RLU=relative luciferase units.

Interpretation of Data Analog 16, DO-REVA

VDR binding, HL60 cell differentiation, and transcription activity. DO-REVA ($K_i$=unknown) has much lower ability than the natural hormone 1α,25-dihydroxyvitamin $D_3$ ($K_i$=2×10$^{-11}$ M) in its ability to compete with [$^3$H]-1,25(OH)$_2$D$_3$ for binding to the full-length recombinant rat vitamin D receptor (FIG. 1). DO-REVA has essentially little to no binding affinity for the VDR. DO-REVA ($EC_{50}$=>10$^{-6}$M) is also considerably lower in its ability to promote HL-60 cell differentiation as compared to 1α,25-dihydroxyvitamin $D_3$ ($EC_{50}$=2×10$^{-9}$M) (See FIG. 2). DO-REVA has little to no ability to induce differentiation of human promyelocyte HL-60 cells into monocytes as compared to the natural hormone (FIG. 2). Also, compound DO-REVA ($EC_{50}$=>10$^{-6}$M) has much lower transcriptional activity in bone cells than 1α,25-dihydroxyvitamin $D_3$ ($EC_{50}$=2.0×10$^{-10}$M) (see FIG. 3). Thus, DO-REVA has weak transcriptional activity, indicated in the 24-hydroxylase (CYP-24) promoter driving luciferase reporter gene system, but does have measurable transcription activity at the higher concentrations tested (see FIG. 3).

These results illustrate that DO-REVA is a candidate for the treatment of or prevention of a cancer especially leukemia, colon cancer, breast cancer, skin cancer or prostate cancer. DO-REVA is a candidate for treating cancer because: (1) it has some VDR binding, transcription activity and cellular differentiation activity; and (2) it is easily synthesized.

Interpretation of Data Analog 15, DO-REVB

VDR binding, HL60 cell differentiation, and transcription activity. DO-REVB ($K_i$=2×10$^{-9}$M) has lower ability than the natural hormone 1α,25-dihydroxyvitamin $D_3$ ($K_i$=2×10$^{-11}$M) in its ability to compete with [$^3$H]-1,25(OH)$_2$D$_3$ for binding to the full-length recombinant rat vitamin D receptor (FIG. 1). DO-REVB is about 2 logs, or 20 times, less potent than 1,25-(OH)$_2$D$_3$ in its affinity for the VDR. DO-REVB ($EC_{50}$=3×10$^{-8}$M) is also lower in its ability to promote HL-60 cell differentiation as compared to 1α,25-dihydroxyvitamin $D_3$ ($EC_{50}$=2×10$^{-9}$M) (See FIG. 2). The ability of the vitamin DO-REVB to induce differentiation of human promyelocyte HL-60 cells into monocytes is about 1 log, or 10 times, less potent than the natural hormone (FIG. 2). Also, compound DO-REVB ($EC_{50}$=1×10$^{-8}$M) has lower transcriptional activity in bone cells than 1α,25-dihydroxyvitamin $D_3$ ($EC_{50}$=2.0×10$^{-10}$M) (see FIG. 3). Thus DO-REVB has weak transcriptional activity, indicated in the 24-hydroxylase (CYP-24) promoter driving luciferase reporter gene system, and is about 2 logs, or 20 times less potent than 1,25-(OH)$_2$D$_3$ in increasing transcription of the 24-hydroxylase gene (see FIG. 3).

These results illustrate that DO-REVB is a candidate for the treatment of or prevention of a cancer, especially leukemia, colon cancer, breast cancer, skin cancer or prostate cancer. DO-REVB is a candidate for treating cancer because: (1) it has some VDR binding, transcription activity and cellular differentiation activity; and (2) it is easily synthesized.

For prevention and/or treatment purposes, the compounds of this invention defined by formula I and II, particularly DO-REVA and DO-REVB, may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds of formula I and II, and particularly DO-REVA and DO-REVB, may be administered orally, topically, parenterally, rectally, nasally, sublingually or transdermally. The compound is advantageously administered by injection or by intravenous infusion or suitable sterile solutions, or in the form of liquid or solid doses via the alimentary canal, or in the form of creams, ointments, patches, or similar vehicles suitable for transdermal applications. A dose of from 0.01 μg to 1000 μg per day of the compounds I and/or II, particularly DO-REVA or DO-REVB, preferably from about 0.1 μg to about 500 μg per day, is appropriate for prevention and/or treatment purposes, such dose being adjusted according to the disease to be treated, its severity and the response of the subject as is well understood in the art. Since the compound exhibits specificity of action, each may be suitably administered alone, or together with graded doses of another active vitamin D compound—e.g. 1α-hydroxyvitamin $D_2$ or $D_3$, or 1α,25-dihydroxyvitamin D₃- in situations where different degrees of bone mineral mobilization and calcium transport stimulation is found to be advantageous.

Compositions for use in the above-mentioned treatments comprise an effective amount of the compounds I and II, particularly DO-REVA and DO-REVB, as defined by the above formula I, Ia, II and IIa as the active ingredient, and a suitable carrier. An effective amount of such compound for use in accordance with this invention is from about 0.01 μg to about 1000 μg per gm of composition, preferably from about 0.1 μg to about 500 μg per gram of composition, and may be administered topically, transdermally, orally, rectally, nasally, sublingually, or parenterally in dosages of from about 0.01 μg/day to about 1000 μg/day, and preferably from about 0.1 μg/day to about 500 μg/day.

The compounds I and II, particularly DO-REVA and DO-REVB, may be formulated as creams, lotions, ointments, topical patches, pills, capsules or tablets, suppositories, aerosols, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds I and II, particularly DO-REVA and DO-REVB, may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

We claim:

1. A compound having the formula:

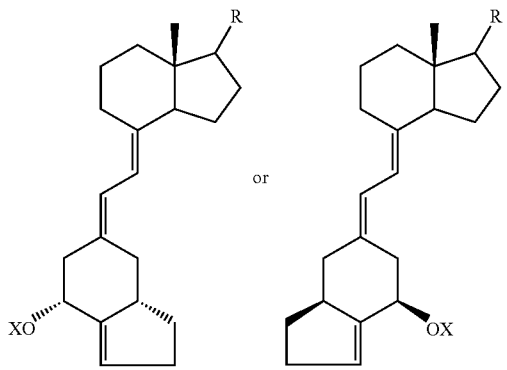

where X is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —CH₂OY, —C≡CY and —CH═CHY, where the double bond in the side chain may have the cis or trans geometry, and where Y is selected from hydrogen, methyl, —COR⁵ and a radical of the structure:

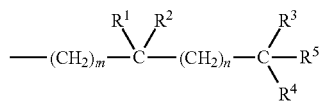

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group having a general formula $C_kH_{2k}$— where k is an integer, the group ═CR²R³, or the group —(CH₂)$_p$—, where p is an integer from 2 to 5, and where $R^3$ and $R^4$, taken together, represent an oxo group, or the group —(CH₂)$_q$—, where q is an integer from 2 to 5, and where $R^5$ represents hydrogen, hydroxy, protected hydroxy, or $C_{1-5}$ alkyl and wherein any of the CH— groups at positions 20, 22, or 23 in the side chain may be replaced by a nitrogen atom, or where any of the groups —CH(CH₃)—, —(CH₂)$_m$—, —CR₁R₂— or —(CH₂)$_n$— at positions 20, 22, and 23, respectively, may be replaced by an oxygen or sulfur atom.

2. The compound of claim 1 wherein X is hydrogen.

3. The compound of claim 1 wherein R is selected from:

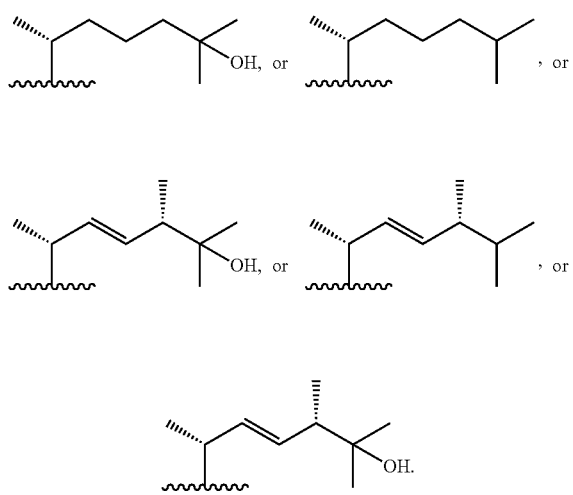

4. A pharmaceutical composition containing an effective amount of at least one compound as claimed in claim 1 together with a pharmaceutically acceptable excipient.

5. The pharmaceutical composition of claim 4 wherein said effective amount comprises from about 0.01 µg to about 1000 µg per gram of composition.

6. The pharmaceutical composition of claim 4 wherein said effective amount comprises from about 0.1 µg to about 500 µg per gram of composition.

7. A compound having the formula:

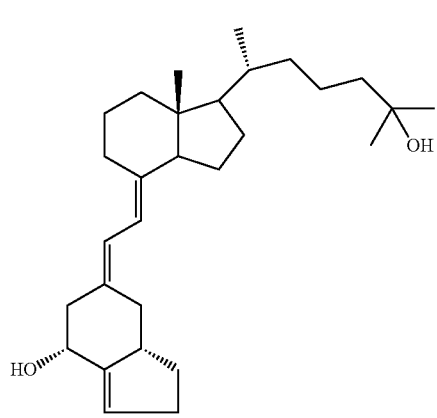

Ia and named 1,2-cyclopentene-25-hydroxy-19-nor-vitamin $D_3$.

8. A pharmaceutical composition containing an effective amount of 1,2-cyclopentene-25-hydroxy-19-nor-vitamin D3 together with a pharmaceutically acceptable excipient.

9. The pharmaceutical composition of claim 8 wherein said effective amount comprises from about 0.01 µg to about 1000 µg per gram of composition.

10. The pharmaceutical composition of claim 8 wherein said effective amount comprises from about 0.1 µg to about 500 µg per gram of composition.

11. A compound having the formula:

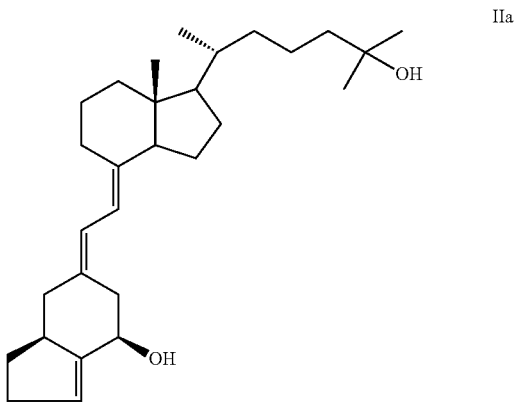

IIa and named 3,2-cyclopentene-1α,25-dihydroxy-19-nor-vitamin $D_3$.

12. A pharmaceutical composition containing an effective amount of 3,2-cyclopentene-1α,25-dihydroxy-19-nor-vitamin $D_3$ together with a pharmaceutically acceptable excipient.

13. The pharmaceutical composition of claim 12 wherein said effective amount comprises from about 0.01 µg to about 1000 µg per gram of composition.

14. The pharmaceutical composition of claim 12 wherein said effective amount comprises from about 0.1 µg to about 500 µg per gram of composition.

15. A method of treating a disease selected from the group consisting of leukemia, colon cancer, breast cancer, skin cancer or prostate cancer comprising administering to a subject with said disease an effective amount of a compound having the formula:

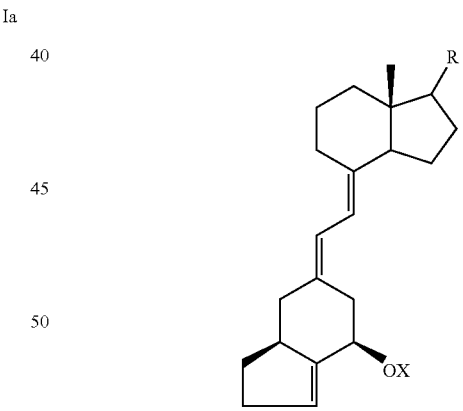

where X is selected from the group consisting of hydrogen and a hydroxy-protecting group, and where the group R represents an alkyl, hydrogen, hydroxyalkyl, or fluoroalkyl group, or R may represent a side chain of the formula:

where Z in the above side chain structure is selected from Y, —OY, —CH$_2$OY, —C≡CY and —CH═CHY, where the double bond in the side chain may have the cis or trans geometry, and where Y is selected from hydrogen, methyl, —COR$^5$ and a radical of the structure:

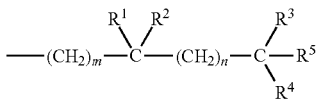

where m and n, independently, represent the integers from 0 to 5, where R$^1$ is selected from hydrogen, deuterium, hydroxy, protected hydroxy, fluoro, trifluoromethyl, and C$_{1-5}$-alkyl, which may be straight chain or branched and, optionally, bear a hydroxy or protected-hydroxy substituent, and where each of R$^2$, R$^3$, and R$^4$, independently, is selected from deuterium, deuteroalkyl, hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group having a general formula C$_k$H$_{2k}$— where k is an integer, the group =CR$^2$R$^3$, or the group —(CH$_2$)$_p$—, where p is an integer from 2 to 5, and where R$^3$ and R$^4$, taken together, represent an oxo group, or the group —(CH$_2$)$_q$—, where q is an integer from 2 to 5, and where R$^5$ represents hydrogen, hydroxy, protected hydroxy, or C$_{1-5}$ alkyl and wherein any of the CH— groups at positions 20, 22, or 23 in the side chain may be replaced by a nitrogen atom, or where any of the groups —CH(CH$_3$)—, —(CH$_2$)$_m$—, —CR$_1$R$_2$— or —(CH$_2$)$_n$— at positions 20, 22, and 23, respectively, may be replaced by an oxygen or sulfur atom.

16. The method of claim 15 wherein the compound is administered orally.

17. The method of claim 15 wherein the compound is administered parenterally.

18. The method of claim 15 wherein the compound is administered transdermally.

19. The method of claim 15 wherein the compound is administered rectally.

20. The method of claim 15 wherein the compound is administered nasally.

21. The method of claim 15 wherein the compound is administered sublingually.

22. The method of claim 15 wherein the compound is administered in a dosage of from about 0.01 μg/day to about 1000 μg/day.

23. The method of claim 15 wherein the compound has the formula:

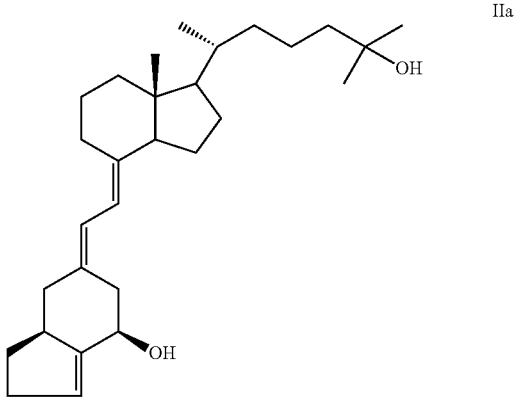

and is named 3,2-cyclopentene-1α,25-dihydroxy-19-nor-vitamin D$_3$.

24. A compound having the formula:

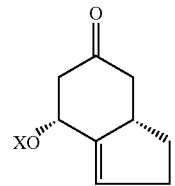

where X is selected from the group consisting of hydrogen and a hydroxy-protecting group.

25. The compound of claim 24 wherein X is hydrogen.

26. The compound of claim 24 wherein X is t-butyldimethylsilyl.

* * * * *